United States Patent [19]

Hussein

[11] Patent Number: 4,762,120

[45] Date of Patent: Aug. 9, 1988

[54] ENDOSCOPIC DEVICE HAVING HANDLE ASSEMBLY AND CATHETER ASSEMBLY

[75] Inventor: Hany M. G. Hussein, Costa Mesa, Calif.

[73] Assignee: Laserscope, Inc., Santa Ana, Calif.

[21] Appl. No.: 59,199

[22] Filed: Jun. 8, 1987

Related U.S. Application Data

[63] Continuation of Ser. No. 756,977, filed as PCT US84/01808 on Nov. 8, 1984, published as WO85/02101 on May 23, 1985, abandoned, which is a continuation-in-part of Ser. No. 549,780, Nov. 8, 1983, abandoned.

[51] Int. Cl.$^4$ .............................................. A61B 1/06
[52] U.S. Cl. ...................................................... 128/6
[58] Field of Search ........................................ 128/4–8, 128/11, 303 R, 303.1, 303.15; 362/32; 403/164, DIG. 4

[56] References Cited

U.S. PATENT DOCUMENTS

| | | | |
|---|---|---|---|
| 2,619,368 | 11/1952 | Anderson | 403/164 |
| 2,691,370 | 10/1954 | Wallace | 128/6 |
| 3,005,452 | 10/1961 | Pitman | 128/11 |
| 3,071,129 | 1/1963 | Wasserman | 128/6 |
| 3,261,350 | 7/1966 | Wallace | 128/6 |
| 3,261,351 | 7/1966 | Wallace | 362/32 |
| 3,866,599 | 2/1975 | Johnson | 128/6 |
| 3,941,121 | 3/1976 | Olinger et al. | 128/6 |
| 4,040,413 | 8/1977 | Ohshiro | 128/6 |
| 4,041,936 | 8/1977 | Carden | 128/6 |
| 4,076,018 | 2/1978 | Heckele | 128/6 |
| 4,146,019 | 3/1979 | Bass et al. | 604/37 |
| 4,157,216 | 1/1979 | Plummer | 128/6 |
| 4,421,106 | 12/1983 | Uehara | 128/4 |
| 4,474,174 | 10/1984 | Petruzzi | 128/4 |
| 4,489,728 | 12/1984 | Matsuo et al. | 128/4 |

FOREIGN PATENT DOCUMENTS

| | | | |
|---|---|---|---|
| 1262502 | 3/1968 | Fed. Rep. of Germany | 128/6 |
| 2062951 | 9/1971 | Fed. Rep. of Germany | 128/6 |
| 1311018 | 3/1973 | United Kingdom | 128/6 |

*Primary Examiner*—Max Hindenburg
*Attorney, Agent, or Firm*—Baker & McKenzie

[57] ABSTRACT

An endoscopic device having a handle assembly and a catheter assembly is disclosed. The catheter assembly carries a viewing conduit which cooperates with an eyepiece on the handle assembly for viewing in a patient's body cavity. The catheter assembly is preferably rotatably and removably mounted on the handle assembly. Also disclosed is a coupling unit which, together with the catheter assembly, forms an endoscopic camera device.

2 Claims, 4 Drawing Sheets

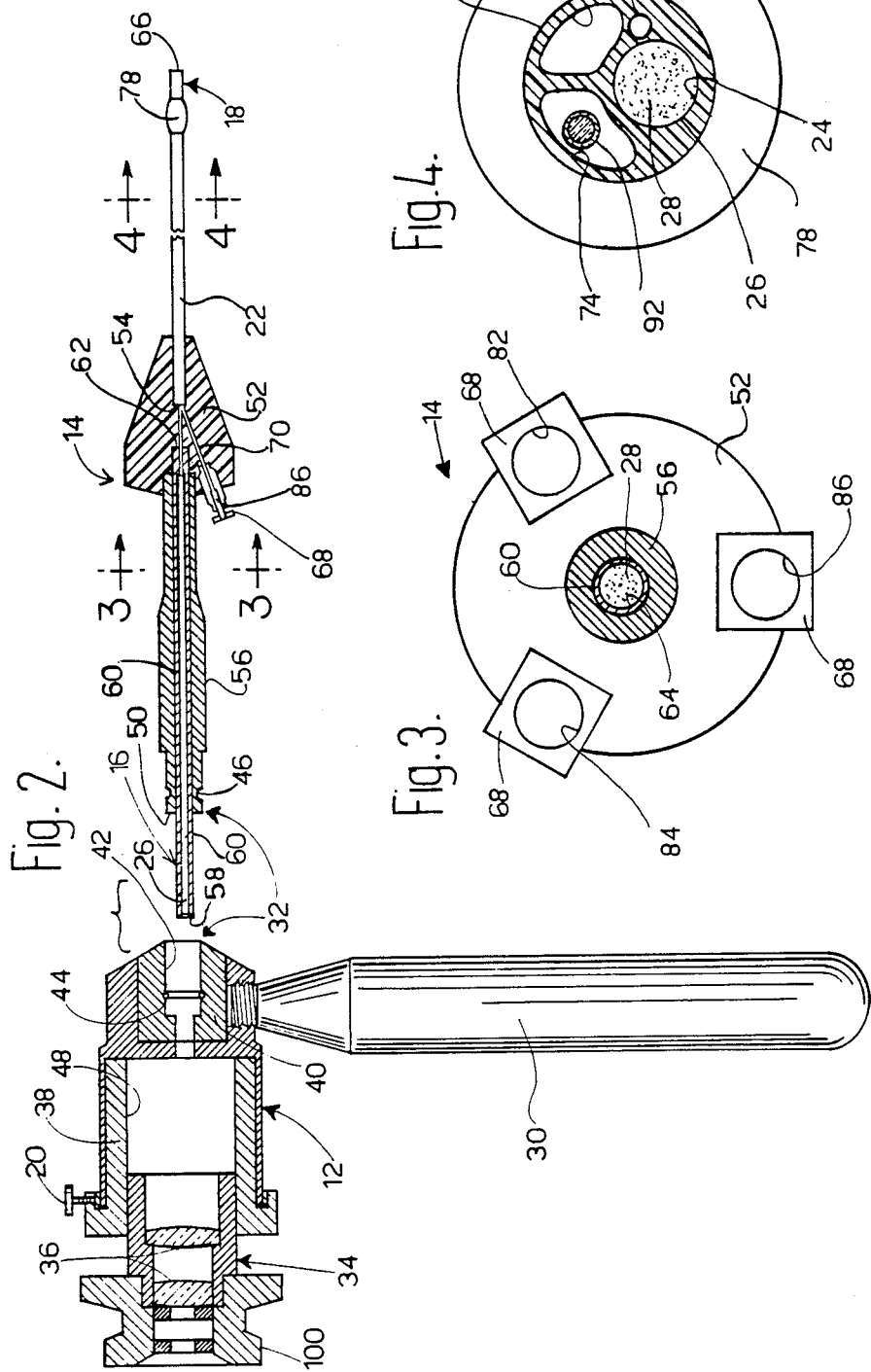

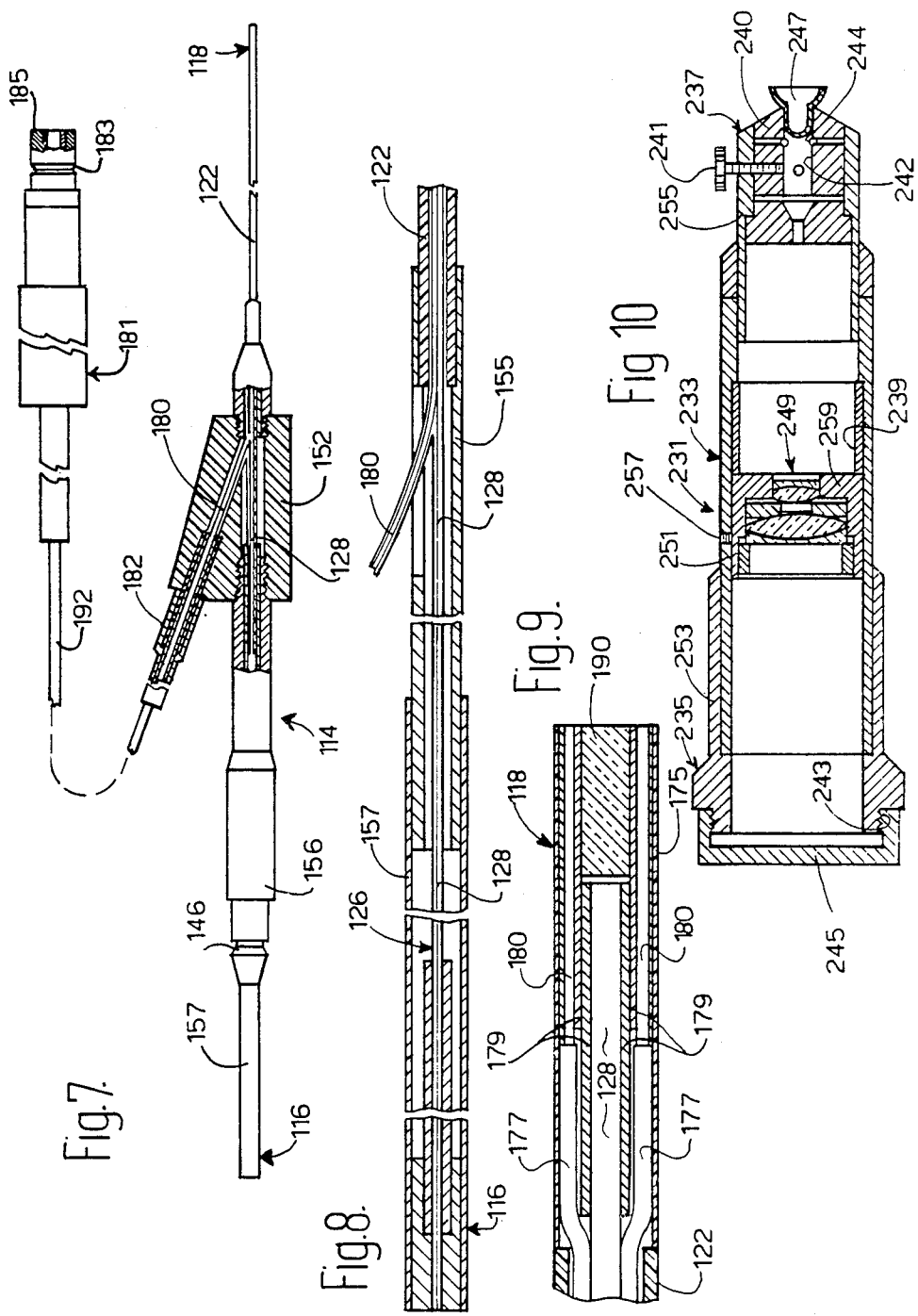

ENDOSCOPIC DEVICE HAVING HANDLE ASSEMBLY AND CATHETER ASSEMBLY

CROSS REFERENCE TO RELATED APPLICATION

This application is a continuation of copending U.S. Pat. application Ser. No. 756,977, filed as PCT US84/01808 on Nov. 8, 1984, published as WO85/02101 on May 23, 1985, now abandoned, which application, in turn, is a continuation-in-part of U.S. Pat. application Ser. No. 549,780, filed on Nov. 8, 1983, now abandoned.

TECHNICAL FIELD OF THE INVENTION

The present invention relates to endoscopic devices having catheter assemblies mounted on handle assemblies.

BACKGROUND OF THE INVENTION

Various kinds of endoscopes are commonly used for examination and treatment within a patient's body cavity. Endoscopes generally have a tubular portion which is inserted into a patient's body cavity and a handle portion which remains outside the patient to be manipulated by a physician. The tubular portion typically carries a fiberoptic viewing bundle which cooperates with an eyepiece in the handle portion to permit viewing within the body cavity. The spacing between the end of the viewing bundle and the eyepiece must be exact for proper focus. A single optical fiber is usually also provided for illumination. Typical of such endoscopic devices are U.S. Pat. Nos. 4,146,019 to Bass et al., 4,163,148 to Fritsche et al., and 3,818,902 to Kinoshita et al.

All of these endoscopic devices suffer from the same drawback. The tubular portion of the device which carries the fiberoptic viewing bundle is fixed on the handle portion. The entire endoscopic device must be sterilized before the tubular portion can be inserted into a patient. Because of the sensitive nature of the optics carried by the eyepiece, steam sterilization and immersion is not possible and ethylene oxide gas is usually used. This requires a longer sterilization time making the entire instrument unavailable for use during this time.

Having the tubular portion fixed on the handle portion has another disadvantage. Viewing bundles and optical fibers are rather delicate and the tubular portion is usually bent as it is inserted into the patient. This places substantial tension and compression forces on the bundle and fibers. After a substantial amount of use, many of the individual fibers making up the viewing bundle begin to break, obstructing viewing. Similarly, a single optical fiber as used for illumination can also break, preventing its use.

Eventually the viewing bundle or optical fiber must be replaced. However, since they are fixed along their entire length within the tubular portion, removal from the tubular portion is difficult if not impossible. The tubular portion in turn is fixed on the handle portion to provide the proper spacing between the bundle end and the eyepiece. This makes replacement of a bundle even more difficult. Often, the entire device is disposed of, or requires factory service.

Many endoscopes also include one or more channels for introducing a flushing liquid into the patient's body cavity. These flushing channels communicate with connectors mounted on the handle portion of the device adjacent the eyepiece. When there is any leakage of liquid from these channels or connectors on the handle portion, the optical system in the eyepiece can be damaged, if not destroyed.

Another common problem with present endoscopes is that rotation of the handle portion also causes rotation of the tubular portion. Movement of the handle portion may be inadvertant or to provide a better grip for the physician. Rotation of the tubular portion in a body lumen can damage the lumen and move the end of the endoscope away from the tissue being studied.

It is also desirable to photograph the image seen through the endoscope to provide a record and allow for further study. The present devices are generally adapters which mount a camera on the existing eyepiece. Unfortunately, this is a rather bulky combination that can be difficult to handle. Placing an adapter on the existing eyepiece also adds additional lenses which further reduces the light transmission through the entire combination. This can limit the photography that is possible depending on the lighting conditions.

Accordingly, what is needed is an endoscopic device which allows for relatively easy replacement of a viewing conduit or optical fiber which may be damaged through use. That portion of the device which comes in contact with the patient should be separately sterilizable to avoid damage to eyepiece optics. The endoscopic device should also separate any fluid channels from the eyepiece optics to avoid damage from leakage and for ease of use. In addition, the device should minimize breakage of optical fibers from flexing and bending of the tubular portion of the device and permit rotation of the handle portion without moving the tubular portion. The present invention meets these desires.

SUMMARY OF THE INVENTION

The present invention is directed to an endoscopic device for viewing and possibly treating tissue within a body cavity of a patient and to an endoscopic camera device for use with a camera body. The endoscopic device can be introduced into a body cavity such as a lumen, and the inside of the lumen viewed and possibly treated with laser irradiation or photographed. A clear flushing fluid may be introduced if desired.

The endoscopic device of the present invention generally includes a handle assembly and a catheter assembly. The handle assembly has an eyepiece which includes focusing optics as used in art. The catheter assembly includes a viewing conduit such as a fiberoptic viewing bundle carried by a cannula. Retaining means mounts the catheter assembly on the handle assembly with the viewing conduit operably associated with the eyepiece.

The catheter assembly is preferably rotatably and removably mounted on the handle assembly. The catheter assembly can then be easily detached and separately disinfected or sterilized without subjecting the handle assembly and eyepiece to sterilization. Alternatively, the catheter assembly can be easily replaced such as when the viewing conduit becomes damaged through use. Several catheter assemblies can be maintained sterile for use in seriatim by the same handle assembly. A rotatable mounting allows the handle assembly to be easily turned without displacing the catheter assembly and damaging tissue within the patient.

In one embodiment of the endoscopic device, a flexible light transmitting conduit such as an optical fiber is slidably received in a channel defined by the flexible cannula. This conduit can be used to transmit illuminating light or laser irradiation for use in the patient's body cavity. Locking means on the cannula fixes a portion of the conduit relative to the cannula. The locking means is preferably at the proximal end of the cannula outside the patient. As the cannula is twisted and bent by insertion into the patient, the remainder of the optical fiber slides relative to the cannula, thus avoiding strain or compression of the fiber. This substantially minimizes fiber breakage commonly caused by bending of the cannula.

The cannula also preferably defines one or more channels through which a flushing fluid or vacuum can be introduced. The channels communicate with respective ports mounted on the catheter assembly. Since the ports are mounted on the catheter assembly and not the handle assembly, any leakage about the ports or from the channels will not damage the eyepiece optics in the handle assembly. The catheter assembly can also be easily replaced should one of the channels become permanently clogged.

The present invention also includes an endoscopic camera device which permits either photographing or video taping within the patient's body cavity. The endoscopic camera device uses the catheter assembly as described above. However, instead of mounting the handle assembly on the catheter assembly, a coupling unit attached to a camera body is mounted on the catheter assembly. The handle assembly can first be mounted on the catheter assembly to guide the end of catheter assembly to its desired location while the operator views through the handle assembly eyepiece. The handle assembly can then be easily removed and replaced by the coupling unit to allow for photography.

The coupling unit includes a housing having a proximal end and a distal end. The distal end defines the socket which receives the catheter assembly. The proximal end includes mounting means for associating the coupling unit with the camera body. The camera body includes imaging means such as photographic film or a video imaging tube.

Because the coupling unit is mounted directly on the catheter assembly, it is not necessary for the light to also pass through the eyepiece on its way to the camera body. This reduces light loss that would be caused by the lenses in the eyepiece. Mounting the camera or camera body on the catheter assembly also becomes less bulky simplifying photography.

Numerous other advantages and features of the present invention will become readily apparent to those skilled in the art from the following detailed description of the preferred embodiment of the invention, the drawings, and the appended claims.

BRIEF DESCRIPTION OF THE DRAWINGS

FIG. 2 is a side elevational exploded view, partially in section, of the endoscopic device of FIG. 1 showing the catheter assembly separated from the handle assembly;

FIG. 3 is a cross-sectional view of the catheter assembly taken generally along plane 3—3 of FIG. 2;

FIG. 4 is an enlarged cross-sectional view of the catheter assembly taken generally along plane 4—4 of FIG. 2;

FIG. 7 is a side elevational view, partially in section, of an alternative embodiment for the catheter assembly;

FIG. 8 is a side elevational view, partially in section, of the proximal end of the catheter assembly of FIG. 7;

FIG. 9 is a side elevational view, partially in section, of the distal end of the catheter assembly of FIG. 7; and FIG. 10 is a side elevational view taken in section of a coupling unit of the present invention.

DETAILED DESCRIPTION OF THE PREFERRED EMBODIMENTS

Figure 1:
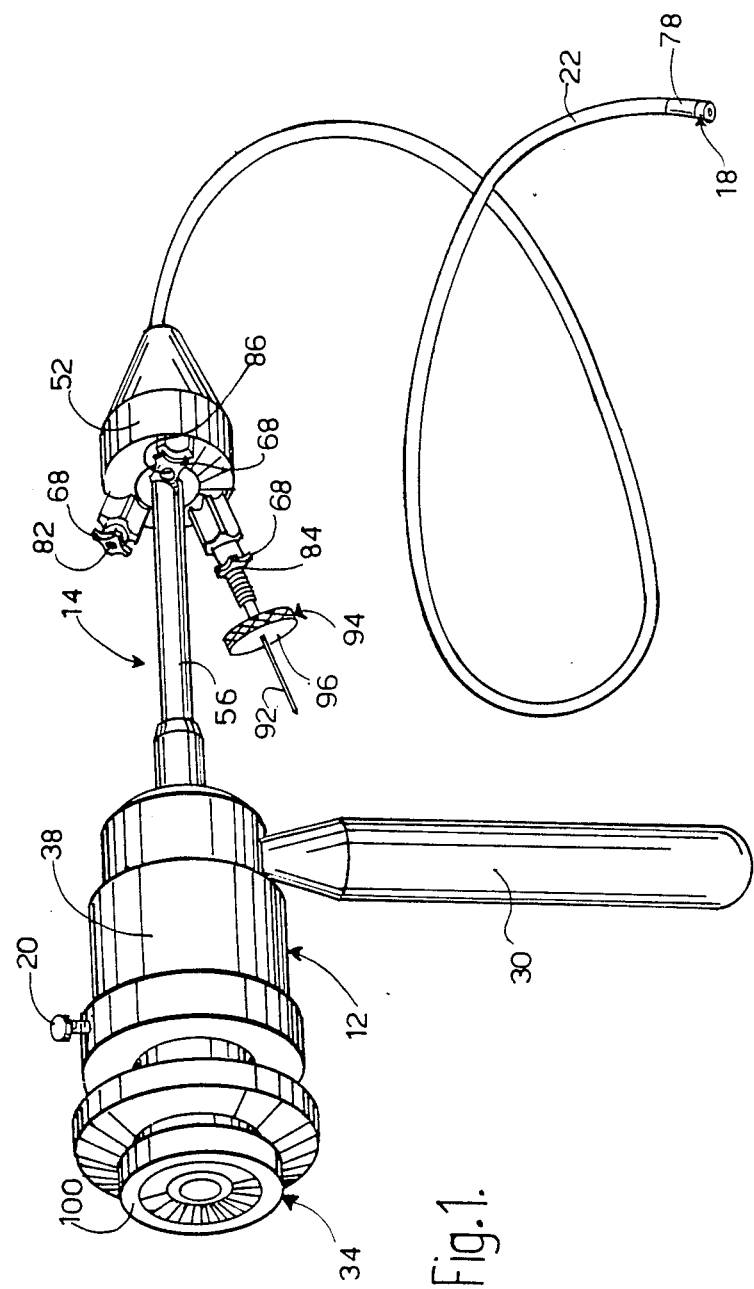
FIG. 1 is a perspective view showing an endoscopic device of the present invention having a catheter assembly mounted on a handle assembly.

While this invention can be embodied in many different forms, there is shown in the drawings and described in detail, preferred embodiments of the invention. The present disclosure is an exemplification of the principals of the invention and is not intended to limit the invention to the embodiments illustrated.

Referring to FIGS. 1 and 2 of the drawings, one embodiment of the present invention, an endoscopic device is shown. The device includes a handle assembly 12 and a catheter assembly 14 having a proximal portion 16 and a distal portion 18. Referring also to FIGS. 3 and 4, the catheter assembly 14 also includes a cannula 22 which defines a passageway 24 into which a viewing conduit 26 such as a coherent fiberoptic bundle 28 is received to be carried by the cannula.

Retaining means 32 are provided for mounting the catheter assembly 14 on the handle assembly 12 with the viewing conduit 26 operably associated with an eyepiece 34 forming part of the handle assembly. The eyepiece 34 includes proximal viewing optics 36 such as a 15× lens system commonly used in endoscopic devices and well known in the art. The eyepiece 34 is preferably adjustably mounted on body portion 38 of the handle assembly 12 to provide for focusing of the optics. This adjustment can be by screw thread or by a sliding carrier as commonly used. Once a proper focus is obtained, the eyepiece 34 can be fixed by locking screw 20.

The retaining means 32 preferably removably and rotatably mounts the catheter assembly 14 on the handle assembly 12. This allows the handle assembly 12 to be rotated for convenience of the physician without rotating of the catheter assembly 14. Alternatively, the catheter assembly 14 can be rotated as it is inserted into a body lumen without also having to rotate the handle assembly. This provides for easier optical tracking during insertion. The catheter assembly 14 can also be easily removed for separate sterilization or replacement should the viewing conduit 26 become damaged through use. The catheter assembly 14 can be sterilized by ethylene oxide gas or by immersion in a disinfectant. Only the exterior of the handle assembly 12 need be sterilized or alternatively wrapped in a sterile covering. This extends the life of the handle assembly 12 and its optics 36 and allows for faster sterilization of the catheter assembly 14.

Having the catheter assembly 14 separable from the handle assembly 12 also allows the viewing conduit 26 to be easily replaced should it become damaged through extensive use. One need only disconnect the old catheter assembly and replace it with a new catheter assembly. The retaining means 32 will automatically align the new viewing conduit with the eyepiece 34.

The handle assembly 12 can also be provided with a handle 30 which extends transversely to the body portion 38 and hence the viewing system. The handle 30 provides a grip for the physician and gives a longer working length for the device. Unlike prior devices, no portion of the catheter assembly and viewing bundle is wasted to provide a holding surface for the physician. This is important since viewing bundles are usually limited in length and certain procedures require the device to be inserted through several arteries, such as from the leg to the heart.

The retaining means 32 preferably includes a socket 42 defined by an insert 40 of the handle assembly 12 into which the proximal portion 16 of the catheter assembly 14 is received. The socket 42 is preferably right-cylindrical in shape. The retaining means 32 can also include a detent such as a snap ring 44 carried within the socket 42. The snap ring 44 is received in a circumferential groove 46 defined by the proximal portion 16 of the catheter assembly 14. Alternatively, the snap ring can be carried by the catheter assembly 14 with the groove on the handle assembly 12. This provides for both rotation and detachable maintenance of the cathether assembly 14.

In addition to the cannula 22, the catheter assembly 14 can also include a plug 52 which is mounted on proximal end 54 of the cannula 22 vicinal or near the cathether assembly proximal portion 16. The plug 52 should be spaced from the handle assembly 12 when the catheter assembly 14 is mounted on the handle assembly. The catheter assembly 14 can also include a sleeve 56 having a proximal end 58 and a distal end 62 which is mounted on the plug 52. The sleeve 56 defines a bore 64 which is in fluid communication with the passageway 24 defined by the cannula 22. This provides a passageway between the proximal end 58 of the sleeve 56 through to distal end 66 of the cannula 22 to retain the viewing conduit 26. As shown, the sleeve 56 defines the groove 46 which cooperates with the detent 44. The sleeve 56 can also include an inner tube 60 which supports the viewing conduit 26 as it extends through the socket into a cavity 48 defined by the body portion 38 of the handle assembly 12.

The viewing conduit 26 is received within the bore 64 and passageway 24 defined by the sleeve 56 and cannula 22 respectfully. The viewing conduit 26, as shown, preferably terminates slightly within the inner tube 60, before the sleeve proximal end 58. This protects the end of the viewing conduit 26 from being scratched or damaged when the catheter assembly 14 is not mounted on the handle assembly 12. Right-cylindrical abutment surface 50 on the sleeve 56 cooperates with the socket 42 and retaining means 32 to ensure proper and automatic spacing between the terminus of the viewing conduit 26 and the eyepiece 34.

Referring to FIGS. 3 and 4, the cannula 22 preferably defines one or more channels. As shown in FIG. 4, the cannula 22 defines three channels 72, 74, and 76. These channels are in fluid communication with respective ports 82, 84, and 86 mounted on the cannula by the plug 52 as shown in FIG. 3. The channels extend at least a major portion of the length of the cannula 22 and in some cases extend between the proximal end 54 and distal end 66 of the cannula. The channels can be used for several purposes. They can be used to introduce a flushing fluid through the distal portion 18 of the catheter assembly 14, to allow for insertion of a medical instrument through the catheter assembly, or allow for the inflation of an expandable balloon 78 carried on the distal portion of the catheter assembly 14.

A plurality of channels can be used at the same time. For example, one channel 76 can be used to expand the balloon 78 while another, second channel 72 is used for flushing or vacuum. Spacing the ports 82, 84 and 86 away from the handle assembly 12 keeps any flushing tubes and other conduits away from the handle assembly 12, allowing easier use of the viewing system.

The balloon 78 is inflated by passing a fluid such as saline through channel 76. The fluid, usually 4 to 10 milliliters of saline or carbon dioxide, enters the balloon 78 through holes 88 in the side wall of the cannula. The desired inflated diameter of the balloon 78 can be determined by the volume of fluid injected. The expandable balloon 78 can be made of any suitable flexible plastic material such as silicone rubber.

Generally, a multiple lumen cannula such as cannula 22 having a plurality of lumens such as channels 72, 74 and 76 as well as passageway 24 is used. The cannula 22 can be any suitable flexible material, but polyurethane is preferred since it minimizes kinking. The cannula 22 should, at least in part, be radiopaque to permit fluoroscopic tracking. In the embodiment shown, the cannula 22 has a diameter of about 2.5 millimeters, channel 76 has a diameter of about 0.3 millimeters and channels 72 and 74 have diameters of about 0.7 to 0.8 millimeters.

The ports 82, 84, and 86 are each provided with a small metal tube 70 one end of which is connected to a fluid coupling 68 and the other end of which is inserted in an interference fit into respective channels 72, 74, and 76. The inner tube 60 forming part of the sleeve 56 is then inserted in an interference fit into the passageway 24. The viewing conduit 26 is then located in the sleeve bore 64 and passageway 24. The sleeve 56, cannula 22, couplings 68 and tubes 70 are located into a mold and the plug 52 cast about these components. An epoxy resin such as RF-5407 Resin Formulators Co., of Culver City, Calif. has been found to be a satisfactory material for molding the plug 52. Other suitable molding materials can also be used. Any leakage of liquid from a port or channel will not damage the optics 36 carried by the handle assembly 12. Since the openings from ports 82, 84 and 86 through the channels 72, 74 and 76 are relatively straight, the channels can be easily unclogged with a wire if necessary.

As shown, channel 76, which can be relatively small, is in fluid communication with the expandable balloon 78 and port 86. For ease of use, port 86 can be provided with fluid coupling 68 such as a Luer-Lok commonly used in the art. Channels 72 and 74, as shown, open through the distal end 66 of the cannula. The port 82, in fluid communication with channel 72, is also provided with a fluid coupling 68 for connection with a fluid source or vacuum source. This allows for the introduction of a clear flushing fluid to improve viewing within the body cavity or for the removal of debris. A small medical instrument can also be introduced through channel 72 or 74. Channel 72 or 74 can also be used with a guide wire (not shown) to guide the catheter assembly distal portion 18 to a site in a lumen. In large lumens an external guide catheter can be used.

Channel 74 carries a flexible light transmitting conduit which can be either a coherent viewing bundle or as shown, a single optical fiber 92. Optical fiber 92 is slidably received in channel 74 such that it is free for relative movement. As shown in FIG. 1, locking means 94 is provided on port 84 by being mounted on fluid coupling 68 to fix a portion of optical fiber 92 relative to a portion of the cannula 22 e.g., that portion surrounded by the plug 52. For clarity, the locking means 94 is not shown in FIG. 3, but is to be received on port 84.

After optical fiber 92 is inserted into the channel 74 and positioned as desired, the locking means 94 then fixes that portion of the fiber 92 adjacent the locking means. The locking means 94 can be a collapsible collar arrangement such as deformable ring using a hollow thumb nut 96. The deformable ring such as a rubber "O" ring is received within the threaded fluid coupling and the optical fiber 92 threaded through the thumb nut 96, "O" ring and coupling. As the thumb nut 96 is tightened, the ring is compressed to hold the optical fiber 96. Since the ring is deformable and preferably of a relatively soft material such as a rubber, the optical fiber can be removably fixed without fear of damage. Alternatively, a portion of the fiber 92 can be fixed on the cannula distal end 66 with glue or other binder as the locking means. As the flexible cannula 22 is bent into various curves, that portion of the optical fiber 92 which is not fixed is free to slide relative to the cannula 22. This avoids the strain and compression common in prior art devices which often destroys the fiber.

In use, the fiber 92 can serve two purposes. It can be connected to a conventional light source to illuminate the body cavity for viewing through conduit 26. Optical fiber 92 can also be used to transmit laser irradiation through the catheter assembly 14. The catheter assembly 14 is then positioned within the patient's body cavity, aimed using the viewing conduit 26, and laser light transmitted through the conduit 92 to alter or remove tissue. Where a viewing conduit is used in place of the optical fiber 92, distal focusing optics can be mounted on the distal end of the viewing conduit so the conduit can move within the cannula 22 and maintain proper spacing with the distal focusing optics.

The viewing conduit 26 is preferably a fiberoptic viewing bundle 28 carried by the sleeve 56 and cannula 22. The cannula distal end 66 is provided with an appropriate distal focusing lens as known by art. Alternatively, the viewing conduit can be a GRIN system, a thick lens system, or any other suitable system used in the endoscope art. The viewing fiberoptic bundle 28 can be either a coherent glass bundle or alternatively a coherent plastic fiber bundle. The latter is preferred since it is relatively less expensive and allows the entire catheter assembly 14 to be disposable.

Figure 5:
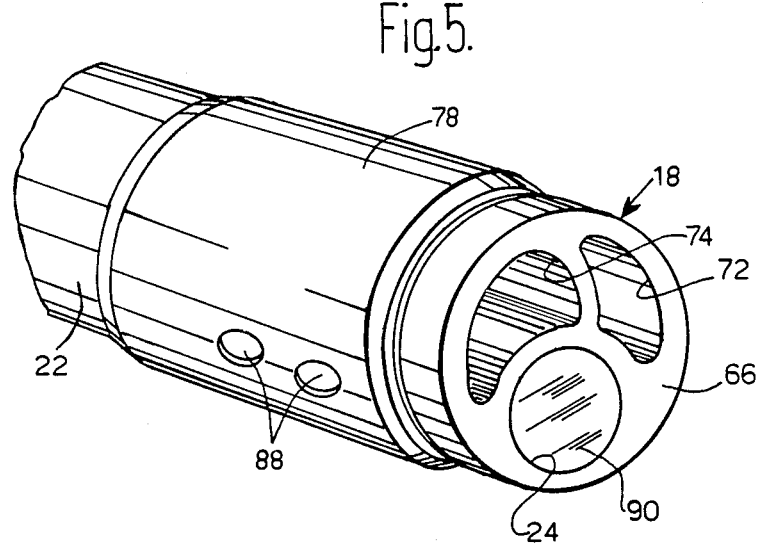
FIG. 5 is an enlarged perspective view of the distal portion of a catheter assembly similar to that of FIG. 1.

The design for the distal portion 18 of the catheter assembly 14 can best be seen in FIG. 5. The shape of the channels 72 and 74 maximizes fluid flow. The distal portion 18 is provided with a GRIN lens 90 mounted in passageway 24 of the cannula. The GRIN lens 90 is chosen and spaced from the viewing bundle 28 to provide for a desired minimum focal length and field of view. In the device shown, the field of view in air is about 55 degrees and the minimum focal length is about 4 millimeters.

The handle assembly 12 is preferably made of a rigid material such as metal or a rigid plastic. The sleeve 56 is also preferably made of a metal such as stainless steel or aluminum. The sleeve bore 64 is then aligned with the cannula passageway 24 and the plug 52 molded about the sleeve distal end 62 and cannula proximal end 54.

Figure 6:
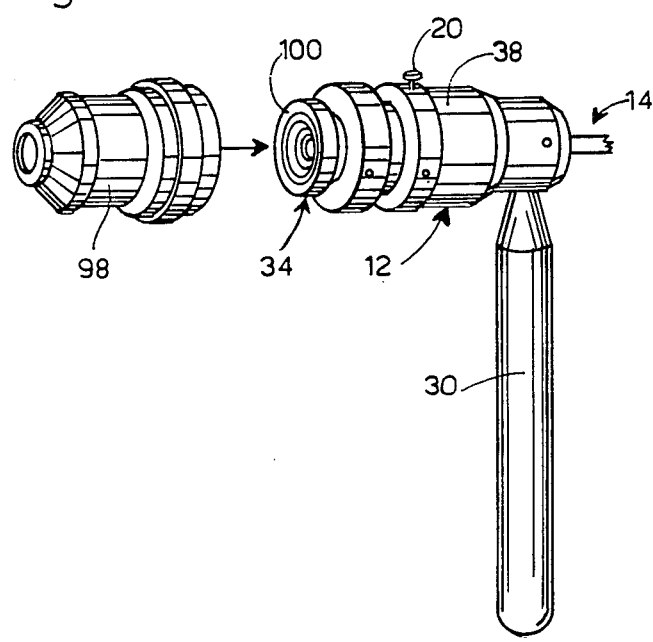
FIG. 6 is a view of the handle assembly of FIG. 2 together with a camera adapter.

Referring to FIG. 6, an adapter 98 can be provided for attaching the device to a television or photographic camera (not shown). The adapter includes an appropriate lens as known in the art. The adapter 98 is mounted on the eyepiece 34 of handle assembly 12 by spring loaded ball bearings within the adapter which coact with flange 100 on the eyepiece 34. The lens of the camera is then mounted on the adapter 98 and the image televised or photographed as desired.

An alternative preferred embodiment for a catheter assembly 114 is shown in FIGS. 7 through 9. The catheter assembly 114 has a proximal portion 116 and distal portion 118. In this embodiment, cannula 122 of catheter assembly 114 is designed to be relatively small in diameter, about 1.7 millimeters. As before, the cannula 122 is associated with sleeve 156 by plug 152. The sleeve 156 having tube 157 on distal proximal portion 116 is much as before. The sleeve 156 includes groove 146 which cooperates with the detent on the handle assembly 12.

The viewing conduit 126 includes viewing fiber optic bundle 128 which extends through the cannula 122 and the sleeve 156. Also provided are light transmitting or illumination fibers 180 which extend through the cannula 122, and exit through port 182 mounted on the plug 152. A metal tube 155 carries the optics through the plug 152. The illumination fibers 180 are connected by conduit 192 to coupling 181 for attachment to an appropriate light source such as a high intensity light. The coupling 181 is provided with appropriate retaining means such as groove 183 on proximal end 185 of the coupling.

Referring also to FIG. 9, the illumination fibers 180 are shown carried by the cannula 122 about the viewing fiber optic bundle 128. A plurality of illumination fibers 180, in design shown, six such fibers, surround the viewing fiber optic bundle 128. The fibers are preferably evenly spaced about the bundle 128.

A lens 190, preferrably a GRIN lens is mounted on the distal portion 118 of the cannula 122 and operably associated with the viewing bundle 128. The illumination fibers 180 extend about the lens 190 and are coterminous with the lens to provide direct emission of light beyond the distal end 118 of the cannula. This design is particularly advantageous since it allows for the construction of a relatively small diameter catheter assembly. The lens 190 is preferably associated with the fiber optic viewing bundle 128 by a ferrule assembly 179 which fixes the relationship of the lens and bundle.

In constructing the cannula and viewing system shown in FIG. 9, the viewing bundle 128 and the illumination fibers 180 are inserted through a tube 123. A two-sleeved ferrule assembly 179 is then placed over the end of the viewing bundle 128 to fix the lens 190 with respect to the viewing bundle. As can be seen in FIG. 9, protective cladding 177 about the illumination fibers 180 is stripped away from that portion of the fibers that extend around the ferrule assembly 179 and lens 190 to minimize the overall diameter of the distal end 118.

In the preferred arrangement, six illumination fibers 180 are located evenly spaced about the viewing bundle 128 and lens 190. The distal end 118 is then filled with an epoxy 175 to seal the distal end with the illumination fibers 180 circling about the lens 190. Using a viewing fiber optic bundle of 0.75 millimeters, the result is a catheter assembly 114 which provides for viewing and illumination while only occupying a diameter of 1.7 millimeters. The catheter assembly 114 can also be preformed, that is the cannula 122 can be given a particular shape such as by placing a bendable wire within the cannula. In use the cannula 122 can be inserted into the patient through a guide catheter to provide access and a passageway for a clear flushing fluid such as saline to improve viewing.

Referring to FIG. 10, a coupling unit 231 of the present invention is shown. The coupling unit 231 can be used with either catheter assembly 14 or 114 to form an endoscopic camera device to be associated with a camera body (not shown). The camera body contains imaging means such as photographic film or a video tube. The coupling unit 231 can either be attached to the camera directly or attached to the camera body through the lens forming part of the camera.

The coupling unit 231 includes a housing 233 having a proximal end 235, a distal end 237 and defining a cavity 239. The distal end 237 defines a socket 242 having the same general configuration as the socket described above for the handle assembly 12. The retaining means can be the same as for the handle assembly 12 including a snap ring 244 within the socket which cooperates with the groove 46 on the catheter assembly 14. As shown, the socket 242 is defined by an insert 240 and the socket is generally right cylindrical. Lock means in the form of a thumb screw 241 is also provided to retain the coupling unit 231 on the catheter assembly 14.

On the proximal end 235 of the coupling unit 231 there is a mounting means for associating the unit with the camera body. The mounting means can be a standard camera screw thread 243 that is protected by a lens cap 245 when the unit is not in use. The socket 242 is similarly protected by a cap 247 when not in use.

The coupling unit 231 also preferably includes optics 249 carried within the cavity 239 on carriage 259 fixed with respect to main tube 251 by set screw 257. The optics 249 enlarge and focus the image on the imaging means carried by the camera body. To allow for adjustable focusing, means are preferably provided for varying the distance between the optics 249 and the socket 242. This is best done by having the housing 233 constituted by the main tube 251, a proximal tube 253 and a distal tube 255. The distal tube 255 is movably mounted on the main tube 251. This movable mounting can be accomplished either by slidably mounting as shown or by appropriate interrelating screw threads as is well known in the art.

In use, the physician uses the catheter assembly 14 and handle assembly 12 to guide the distal end 18 of the catheter assembly to an appropriate location in the patient's body cavity. Once the distal end 18 of the catheter assembly 14 is properly located, the physician can then easily remove the handle assembly 12 from the catheter assembly 14 and replace it with the coupling unit 231. The coupling unit 231 can be premounted on the camera body. It then becomes possible to either video tape or photograph the desired part of the patient's body cavity.

Because the coupling unit 231 does not operate through the eyepiece 34 of the handle assembly 12, there is a minimum amount of light loss. The coupling unit 231 and camera body are also easier to handle since the handle assembly 12 is not present. The relative ease of the interchangeability between the coupling unit 231 and the handle assembly 12 is a particular advantage of the present invention.

The coupling unit 231 can also be provided prefocused and sterile thus avoiding the necessity of a sterile bag which can hamper use. Two or more coupling units 231 can also be used alternatively, one attached to a video camera for viewing by several people and the other attached to a still camera to document the view.

What is claimed is:

1. An endoscopic viewing device comprising:
   (a) a handle assembly including an eyepiece, the handle assembly also defining a socket;
   (b) a flexible cannula having a proximal end and a distal end and defining a passageway and channel between the ends;
   (c) a plug mounted on the cannula proximal end and having a port in fluid communication with the channel;
   (d) a sleeve having a proximal end and a distal end and defining a bore between the ends, the sleeve being mounted on the plug with the bore in communication with the cannula passageway;
   (e) a flexible coherent fiberoptic viewing bundle received in the passageway and bore;
   (f) a flexible light transmitting fiber slidably received in the channel through the port;
   (g) locking means carried by the plug for fixing a portion of the light transmitting fiber with respect to the plug; and
   (h) retaining means for rotatably and releasably mounting the sleeve proximal end in the socket with the viewing bundle operably associated with the eyepiece.

2. The endoscopic viewing device of claim 1 wherein the handle assembly includes a body portion retaining the eyepiece, and a handle; the handle being transverse to the body portion.

* * * * *